United States Patent [19]

Moletta et al.

[11] Patent Number: 5,248,423
[45] Date of Patent: Sep. 28, 1993

[54] PROCESS FOR THE REGULATION OF A DEVICE FOR THE REMOVAL OF POLLUTANTS FROM WASTE WATER

[75] Inventors: Penato Moletta, Narbonne; Jean-Pierre Coudert, Perpignan; Fréderic Ehlinger, Le Pecq, all of France

[73] Assignees: Degremont; Institut National de la Recherche Agronomique; Centre National de la Recherche Scientifique, France

[21] Appl. No.: 833,155

[22] Filed: Feb. 10, 1992

[30] Foreign Application Priority Data

Feb. 11, 1991 [FR] France .................. 91 1542

[51] Int. Cl.$^5$ .............................. C02F 3/28
[52] U.S. Cl. ...................... 210/614; 210/739
[58] Field of Search ............ 210/614, 143, 96.1, 210/85, 739

[56] References Cited

U.S. PATENT DOCUMENTS 4,349,435  9/1982  Ochiai .................. 210/614
4,986,916  1/1991  Hickey .................. 210/614

OTHER PUBLICATIONS

"Enhancement of Anaerobic Treatment Efficiency Through Process Modification," S. R. Harper; Journal WPCF, vol. 59, No. 3, pp. 152–161, Mar. 1987.
Patent Abstracts of Japan, vol. 6, No. 208 (C-130)(1086) Oct. 20, 1982 and JP-A-57-113-899 (Fuji Denki Seizo K.K.) Jul. 15, 1982.
W. R. Slater, "A Microcomputer-based Instrumentation System for anaerobic Wastewater Treatment Processes," Water Research, vol. 24, No. 1, Jan. 1990, Oxford GB, pp. 121–123.

Primary Examiner—Stanley S. Silverman
Assistant Examiner—Neil M. McCarthy
Attorney, Agent, or Firm—Pollock, VandeSande & Priddy

[57] ABSTRACT

This invention relates to a process for the regulation and automatic control of a device for the removal of pollutants from waste water by methane fermentation, which consists of simultaneously measuring, in the gaseous phase in the digesters of a fermentation reactor, the following three parameters: output of gas emanating from the conversion of the organic matter during fermentation, the ratio of the percentages of methane and carbon dioxide and the gaseous hydrogen content, and in then processing in real time the data thus collected in order to obtain signals reflecting the instantaneous state of the ecosystem of the pollutant removal device.

3 Claims, 5 Drawing Sheets

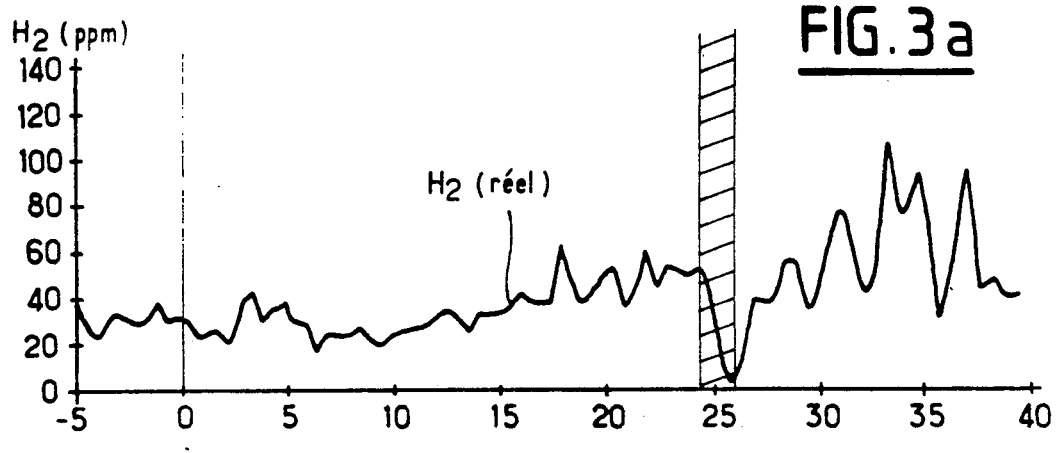
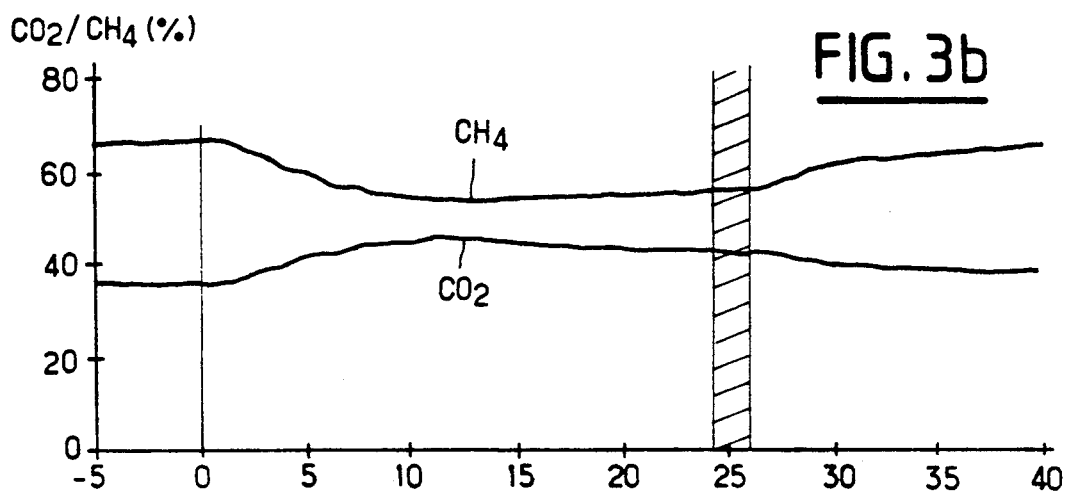
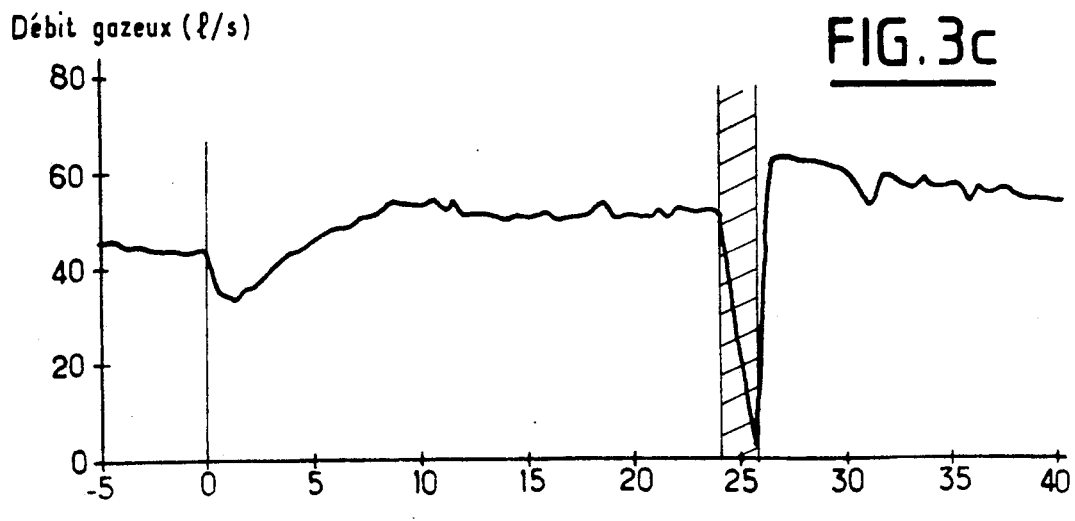

PROCESS FOR THE REGULATION OF A DEVICE FOR THE REMOVAL OF POLLUTANTS FROM WASTE WATER

The present invention relates to a process for the regulation and automatic control of a device for the removal of pollutants from waste water by methane fermentation.

The technique of methane fermentation, which is applied especially to the treatment of agri-foodstuffs effluents, is frequently known to be used as a process for the effective removal of pollutants. Purification processes of this type employ increasingly intensive reactors which enable substantial concentrations of biomass to be confined in very compact volumes. As a result, ecosystems are continually in great demand with a view to working under the limiting conditions which are compatible with a good microbial balance. Optimization of the functioning of such reactors is becoming very difficult and, since the personnel appointed to operate an anaerobic purification plant are not always appropriately trained, it is the case that the pollutant removal device is often working below its capacity for fear of an organic overload.

According to the current art, monitoring of the functioning of anaerobic fermenters depends on the changes occurring in certain parameters such as, in particular, the pH, the buffering power in terms of carbonates and the extent of decline in the chemical oxygen demand (COD), this parameter being considered to represent the disappearance of pollutants. In these installations of known type, measurement of these parameters naturally takes place on the liquid phase in the reactors and with discontinuous sampling.

Now, in view of the characteristic of the anaerobic ecosystem of functioning in successive steps, acidogenesis followed by methanogenesis, pH and COD are not necessarily the most judicious parameters to be measured in regard to the disappearance of pollutants from the pollutant removal installation.

In effect, in a first step, the organic matter is converted to volatile fatty acids through the action of acidogenic bacteria, and then, in a second step, the volatile fatty acids thereby obtained are broken down to methane and carbon dioxide and, as a result, they no longer influence the pH of the medium if the buffering power is sufficient. In contrast, in the case of organic overload, for example, the volatile fatty acids can accumulate and can lower the pH, and the measurements of pH and of COD then reflect a fait accompli, and it is often too late to react when the measured values of these two parameters reach critical thresholds.

Moreover, the pH parameter is reliable on condition, however, that the probes used for the purpose of its determination from the liquid phase in the reactor are frequently and regularly maintained, and this naturally constitutes a step which is often exacting. In addition, measurement of the other two parameters, namely carbonates and COD, demands a minimum of laboratory equipment. In view of the fact that it is appropriate to take samples and then to analyze them, and that the analysis time is very long (taking of the order of 2 hours), only a single measurement at most is generally carried out per day. Moreover, at the present time, on account of the cumbersome nature of the procedure for carrying it out, such an analytical technique does not appear to be capable of automation under conditions of industrial operation. As a result, in the case of organic overload of a reactor, the technician responsible for monitoring the latter does not have at his disposal rapidly detectable and genuinely significant signs of a malfunctioning of the reactor.

Consequently, the present invention had as its objective to provide a new process for the regulation and automatic control of a reactor for the removal of pollutants from waste water by methane fermentation effecting an automatic operation of the anaerobic reactor while optimizing its functioning.

The idea on which the present invention is based consists in continuously measuring three parameters, not in the liquid phase in the reactor as in the prior art, but in the gaseous phase in the digesters.

In 1988 (RENARD et al. "Adaptative control of anaerobic digestion processes: A pilot scale application". Biotechnology and Bioengineering, vol. 31, pages 287–294), an attempt was made to control a laboratory methanisation reactor automatically, the control being based only on the continuous measurement of gas production. Every two hours, a determination of the COD at the inflow and at the outflow of the reactor was necessary, which, as seen above, cannot be capable of implementation on an industrial site.

In 1989 (MOSEY et al. "Patterns of hydrogen in biogas from the anaerobic digestion of milk-sugars". Water Science Technology, vol. 21, pages 187–196), consideration was given to the appropriateness of measuring continuously the hydrogen in the biogas in order to regulate the output of the pump feeding untreated water. The test reactor was fed semi-continuously, thereby involving detention periods of 21 days which are not compatible with industrial practice. The responses from the measurement of the hydrogen in the gas appeared to be insufficient and not always useful for controlling a methanisation reactor efficiently. Other authors have attempted to measure gas production and $CH_4$, $CO_2$ and hydrogen content concomitantly.

However, (SLATER et al. "A microcomputer-based instrumentation system for anaerobic waste water treatment processes". Water Research, 1990, vol. 24, No. 1, pages 121–123), variations in the $CH_4$ and $CO_2$ contents which were appreciable and capable of utilization were not detected, hence no attempt was made to correlate these parameters with one another.

Furthermore, in a study reviewing all processes for the control of fermenters (SWIZENBAUM et al. "Monitoring of the anaerobic methane fermentation process". Enzyme Microbiology and Technology, 1990, vol. 12, pages 722–730), a negative appraisal is to be found in regard to the use of parameters of the type comprising gas production and $CH_4$, $CO_2$ and $H_2$ contents.

In distinction to all these authors, who compared the response of each parameter taken individually, the present applicants directed their attention to the combination of these parameters. On a pilot plant fed with an industrial untreated water, all cases of overloads or of accidents capable of occurring on an industrial installation were simulated. Each case was characterized by a combination of responses derived from the simultaneous measurement of three parameters: gas production, $CH_4/CO_2$ ratios and $H_2$ content of the biogas.

The subject of the present invention is hence a process for the regulation and automatic control of a device for the removal of pollutants from waste water by methane fermentation, characterized in that it consists of simultaneously measuring, in the gaseous phase in the digesters of a fermentation reactor, the following three parameters, namely the output of gas emanating from the conversion of the organic matter during fermentation, the ratio of the percentages of methane and carbon dioxide and the gaseous hydrogen content, and in then processing in real time the data thus collected in order to obtain signals reflecting the instantaneous state of the ecosystem of the pollutant removal device.

According to an embodiment of the process which is the subject of the invention, measurement of the three parameters is performed using sensors which are arranged on the pipe collecting the biogas produced at the outflow of the reactor. According to a variant, these sensors may be arranged on a biogas recycling loop.

According to the invention, the signals thereby obtained from the measurement of the three parameters mentioned above may be used to actuate an alarm, or alternatively to act directly on the waste water feed system of the reactor.

It will be understood that the process which is the subject of the present invention deliberately diverges from the technique used hitherto on industrial sites, since, at the present time, the cumulative daily volume of biogas and the methane/carbon dioxide ratio were considered to be production parameters, that is to say parameters providing a picture of the final state of the reaction. Now, in the process which is the subject of the present invention and as defined above, these parameters are considered to provide an instantaneous picture of the reaction which takes place in the reactors used industrially and functioning according to the homogeneously mixed mode, the gas produced, collected at the outflow of the reactor being an accurate image of the gas confined within the reaction mixture.

Consequently, the parameters measured according to the process of the invention, namely gas output, ratio of the methane/carbon dioxide percentages and gaseous hydrogen, reflect in real time the state of the ecosystem as well as the changes occurring therein. This combination of parameters makes it possible to go beyond the notion of overall fermentation factor and to fathom in depth the physiological state and metabolism of the biomass. The measurement of these three parameters and the processing of the data thus collected make it possible to detect, well upstream of the system, a problem which would not yet be detected using the previous technique mentioned above, that is to say the measurement of the conventional parameters pH, COD and alkalinity. This real-time detection of a malfunctioning of the reactor enables measures to be taken immediately in order to correct these problems, thereby effecting automatic control and automatic regulation of the device.

A number of examples showing how different factors can modify the ecosystem of the reactor, and can hence interfere with the functioning of anaerobic fermentations, are given below. In these examples, which are naturally in no way limiting in nature, the following three factors have been chosen:

1. an organic overload caused by an increase in the concentration of the effluent to be treated;
2. a fall in temperature of the reactor; and
3. a modification of the nature of the pollution of the waste water undergoing treatment.

In the course of this description, reference is made to the attached drawings, wherein:

FIGS. 3a to 3c are curves illustrating the changes in the parameters measured according to the process of the invention during a modification of the nature of the pollution of the untreated water undergoing treatment (Example 3);

EXAMPLE 1

Figure 1A:
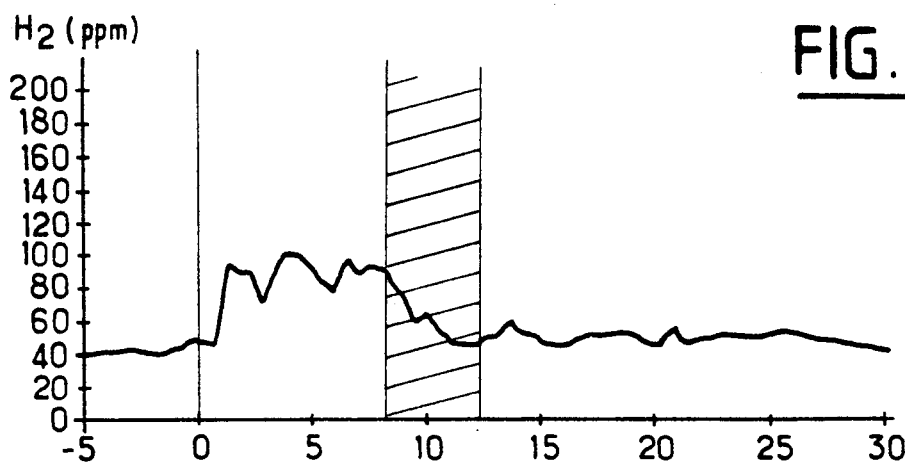
FIGS. 1a to 1c are curves illustrating the changes in the parameters measured according to the process of the invention during an organic overload of the reactor (Example 1)
Figure 1B:
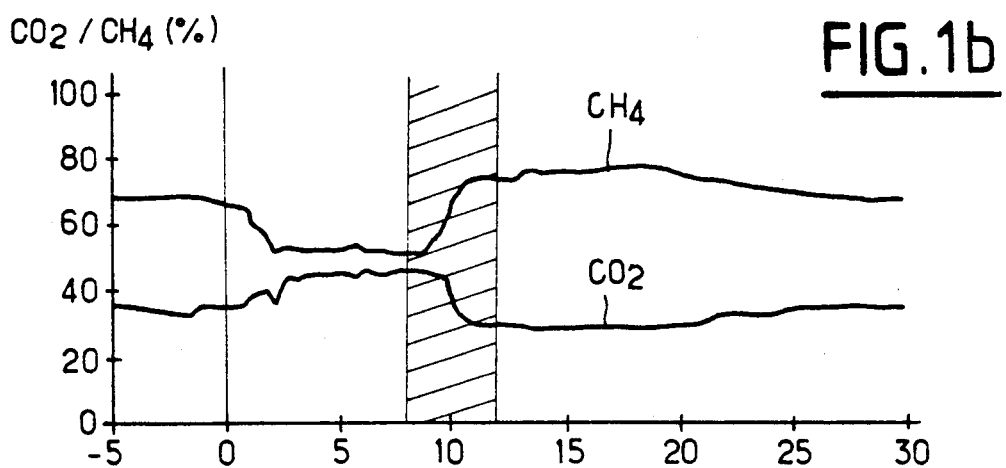
Figure 1C:
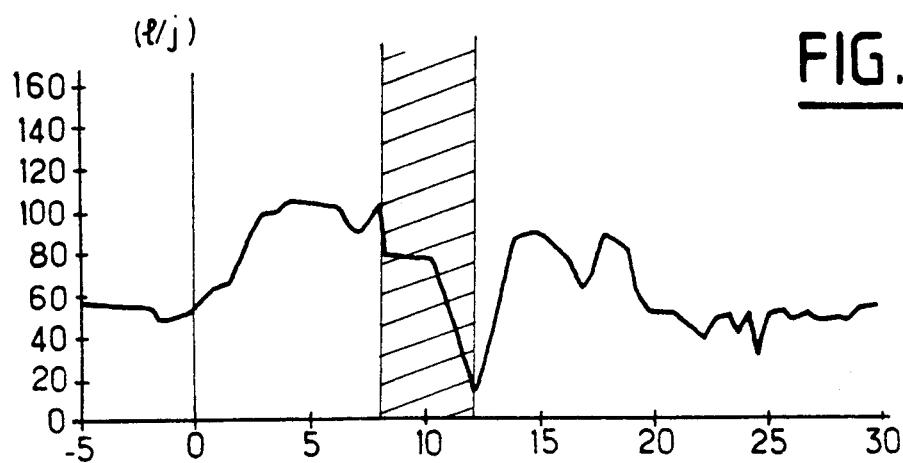

This first example relates to a reactor having a normal feed rate of 20 g per liter of COD, and to which an organic overload, caused by an increase by a factor of 6 in the concentration of the effluent to be treated, is applied over a period of 8 hours. In this example, feeding was stopped from 8 hours to 12 and then reestablished under normal operating conditions. In FIG. 1a, the curve is shown for the gaseous hydrogen content (in ppm) as a function of time, in FIG. 1b, the variations in the ratio percentage of carbon dioxide/percentage of methane are shown as a function of time, and in FIG. 1c, the curve is shown for variation in the gaseous output (in liters per day) as a function of time. Examination of these curves shows that changes in the three parameters already take place one hour after the beginning of overload:

gaseous hydrogen rises from a stable value of 40 ppm to a ceiling value of the order of 100 ppm (equivalent to a 150% increase);

the ratio of the carbon dioxide/methane percentages at the same time varies as a result of a fall in the methane content and an increase in the carbon dioxide content;

the abrupt change in the above two parameters is followed by a downward trend in gas production, three hours after the beginning of the appearance of organic overload.

It is hence seen that, by means of the invention, reproducible conditions signifying an unstable situation of the ecosystem are obtained, and measurement of the three parameters mentioned above and processing of the signals obtained from the data collected from this measurement make it possible to trigger an action performed on the reactor, which action, as specified above and as will be seen below, may consist in triggering an alarm or, in an integrated regulation system, in acting immediately on the rate of feed of the reactor with untreated water.

EXAMPLE 2

Figure 2A:
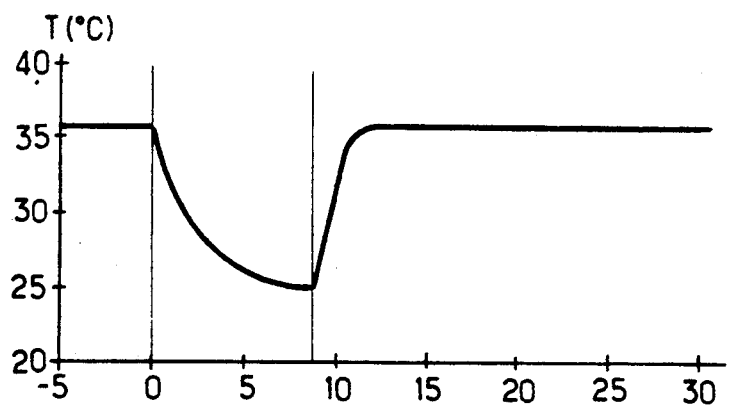
FIGS. 2b to 2d are curves illustrating the changes in the parameters measured according to the process of the invention during a fall in the temperature of the reactor according to the curve in FIG. 2a (Example 2)
Figure 2B:
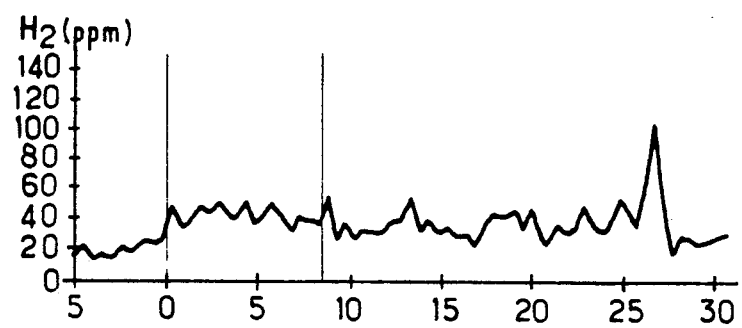
Figure 2C:
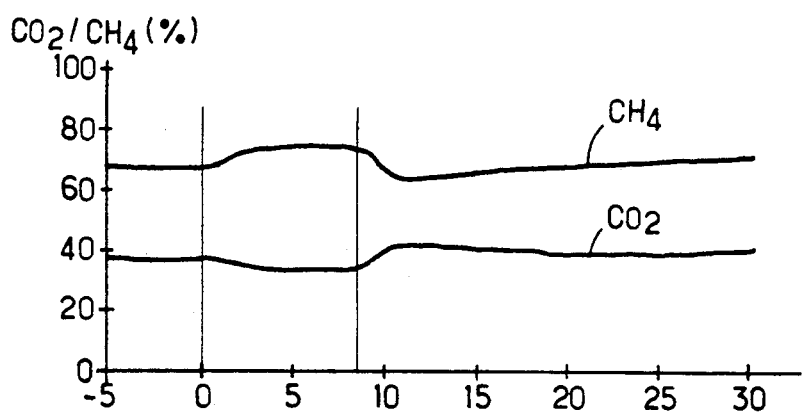
Figure 2D:
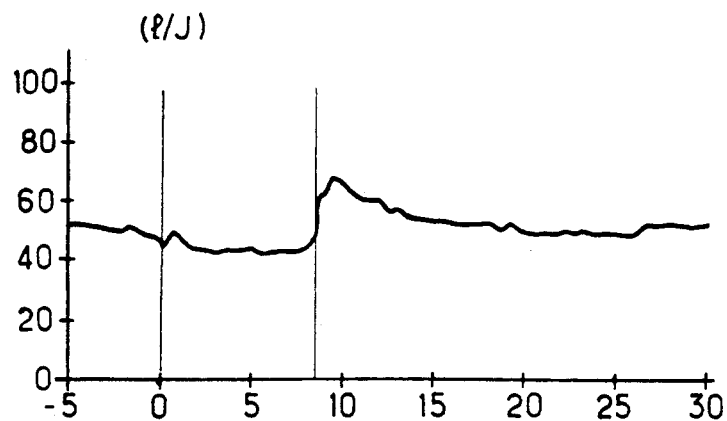

This example relates to the case of a fall in temperature of the reactor in accordance with FIG. 2a. FIGS. 2b, 2c and 2d correspond to FIGS. 1a, 1b and 1c of the previous example, and they hence show the changes with time in the three parameters measured according to the process of the invention:

it is seen (FIG. 2b) that the increase in gaseous hydrogen content is smaller than in the case of Example 1, that is to say during an increase in the concentration of the effluent to be treated;

the methane and carbon dioxide contents change in the opposite direction, that is to say, in this example, the methane content increases while the carbon dioxide content decreases;

the output tends to decrease, which duly reflects a decrease in bacterial activity.

As in the previous example, measurement of these three parameters enables an improper functioning of the reactor to be detected immediately and measures enabling this malfunctioning to be remedied to be taken without delay.

EXAMPLE 3

In this third example, the situation which arises when there is a change in nature of the pollution, that is to say of the effluent undergoing treatment, has been illustrated. In this example, up to 0 hours, the effluent feed consisted of stillage (at a concentration of 20 g per liter of COD), and then from 0 to 24 hours the reactor was fed with glucose according to the same concentration, the feed being stopped from 24 to 26 hours and then resumed using stillage. The treatment of such a problem requires an abrupt adaptation of the bacteria to the new substrate and, in some cases, necessitates growth of a new type of bacterium. The necessary change in the metabolism of the biomass also manifested itself in a change in the three parameters measured by the invention, which change is illustrated in FIGS. 3a to 3c which correspond to FIGS. 1a to 1c:

it is seen that the gaseous hydrogen content (FIG. 3a) appears to increase only very belatedly after the beginning of the admission of a new substrate;

in contrast, it is noted that the gaseous output instantaneously undergoes an abrupt fall linked to the adaptation of the bacteria, and it is then seen that gas production becomes re-established and that it even tends to increase relative to the initial substrate;

the change in the ratio of the carbon dioxide/methane percentages is very rapid as in the previous two cases.

It is hence possible, as in the previous examples, to detect immediately the modification of functioning of the reactor and to take the measures necessary for a return to a normal mode of functioning.

Figure 4:
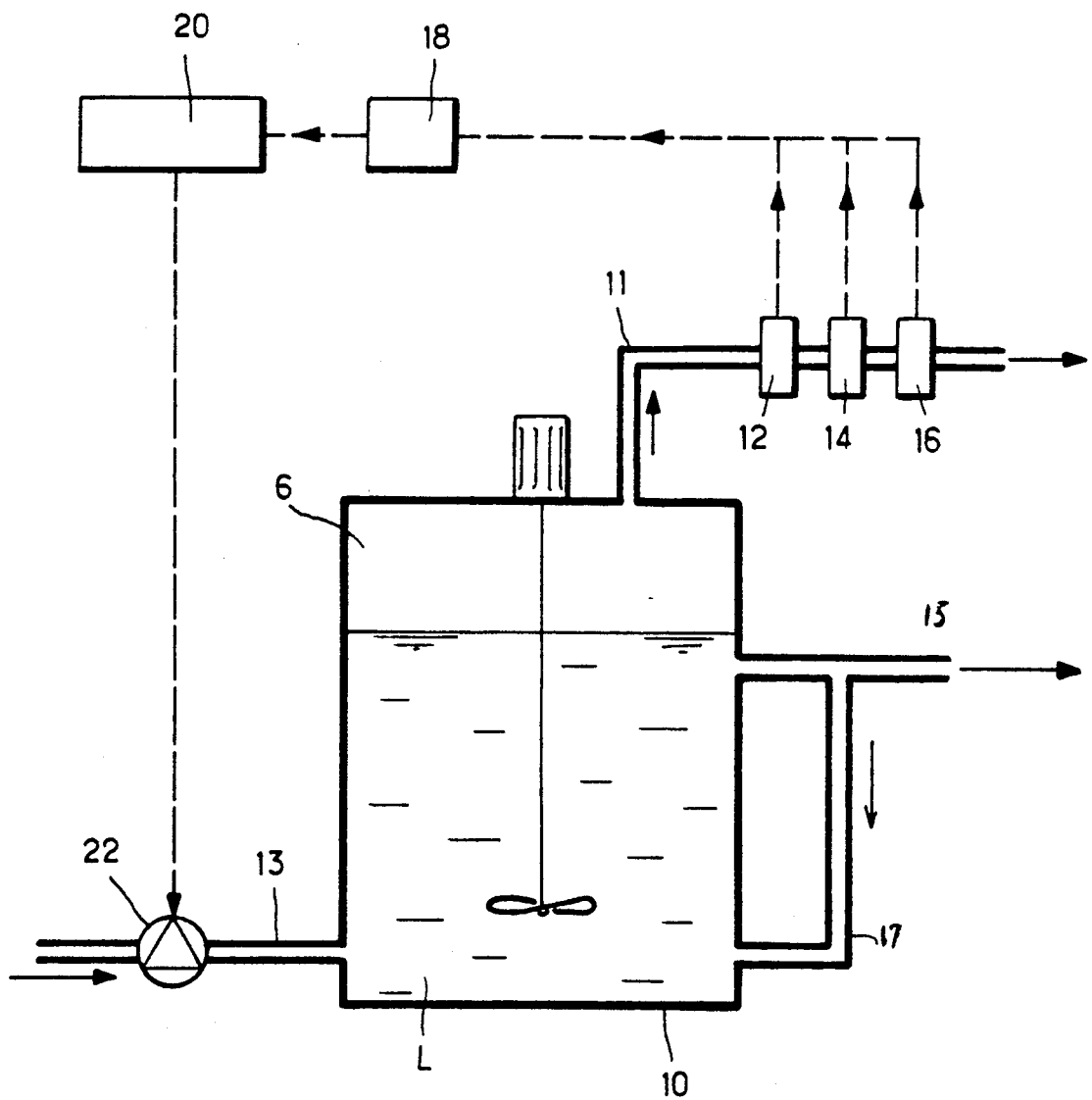
FIG. 4 is a diagrammatic representation of a reactor employing the process which is the subject of the present invention.

Reference is now made to FIG. 4, in which an example of embodiment of a reactor employing the process which is the subject of the invention, as specified above, is shown diagrammatically.

In this Figure, the reactor in operation is seen at 10, with its liquid phase L and its gaseous phase G. The effluent is brought to the base of the reactor via a pipe 13, this feed being controlled using a pump 22, and the treated water is discharged via a pipe 15 on which there is mounted a pipe 17 for recycling a portion of the treated water into the reactor. Reference 11 denotes the biogas outflow pipe, on which, according to the invention, sensors 12, 14, 16 are positioned, making it possible to record in real time data relating, respectively, to the three parameters measured according to the process of the invention: output of gas emanating from the conversion of the organic matter during fermentation, ratio of the percentages of methane and carbon dioxide, and gaseous hydrogen content. The data thus collected may be processed in a central processing unit 18 and the signals obtained from this unit may be used to act on a control system 20 for regulation of the pump 22 feeding waste water. Thus, in this particular and non-limiting embodiment of the process of the invention, a looped regulation may be carried out. According to another embodiment, the data collected from the sensors 12, 14, 16 may be used to actuate an alarm, thereby enabling the technicians responsible for the functioning of the reactor to take the necessary measures to effect a return to normal operating conditions.

By means of the invention, the three parameters are measured continuously on the biogas outflow of the reactor, and the sensors used to obtain the data relating to the changes in these three parameters possess the characteristic of not suffering impairment of function since they are placed in a non-aqueous phase not containing biomass, thereby avoiding any risk of contamination and of drifting of the signals obtained. Thus, the invention offers the operator a reliable and maintenance-free means of monitoring the functioning of a purification plant.

It will be noted that the sensors may be arranged on a biogas recycling loop.

Figure 5:
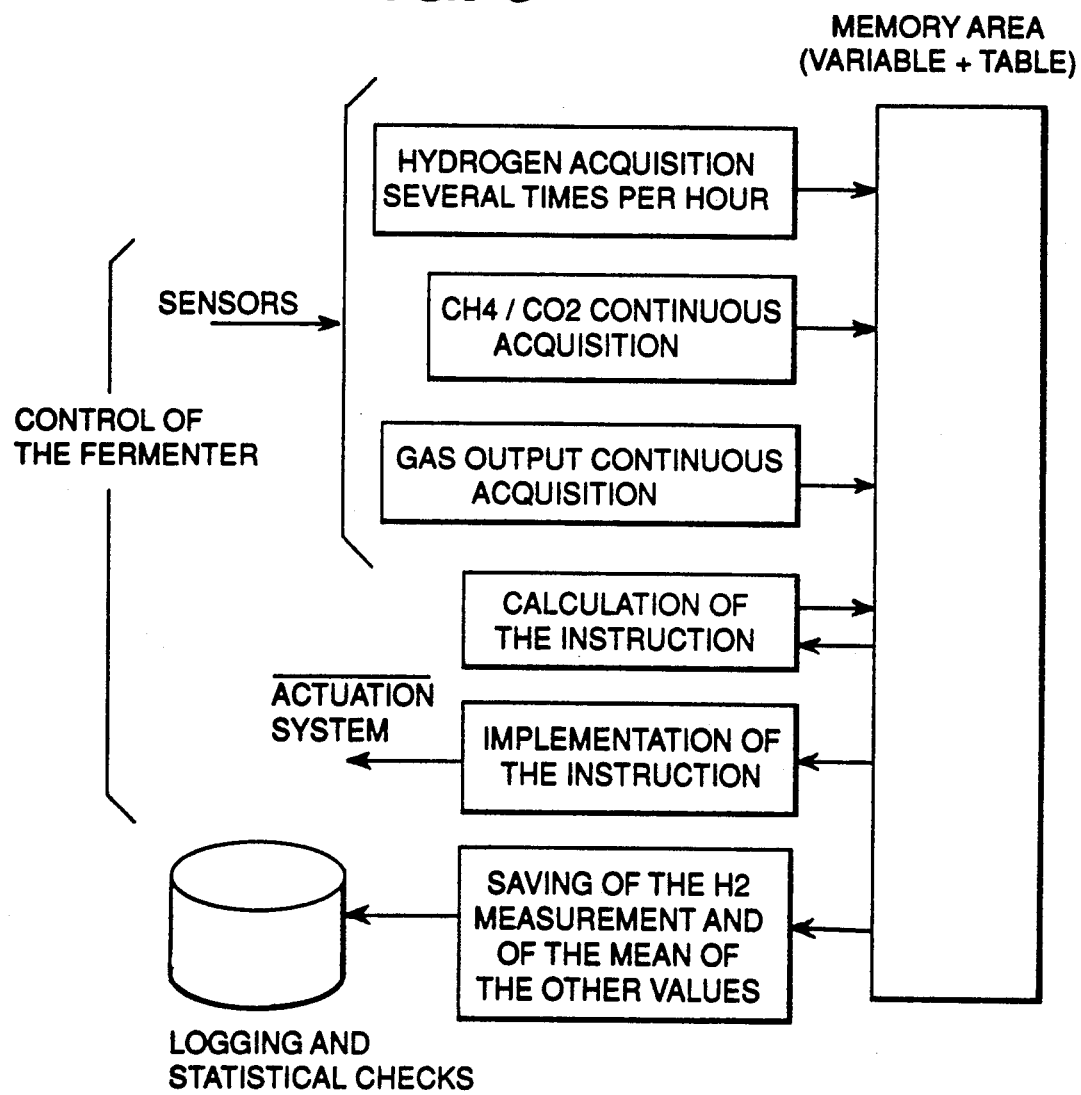
FIG. 5 is a flow diagram illustrating an example of software used for operating the process according to the present invention.

Reference is now made to FIG. 5, which illustrates the flow diagram of software which may be used in processing the data collected from the sensors employed by the invention.

This software, developed in a multitask programming language, is supported by a real-time operating system, the algorithms of the different sensors and also the calculation of the parameters of the implementation instruction, imposing a multiprocess programming in the process of the invention.

Acquisitions take place from the sensors placed in the gas circuit. Two parameters are measured continuously: ratio of the methane/carbon dioxide percentages and gaseous output. On a series of measurements performed at given intervals determined by the biological system and chosen in such a way as to be compatible with the sphere of application, the mean is calculated and then the means for each interval are thereafter compared. Measurement of the gaseous hydrogen content is performed discontinuously at regular intervals. Successive values are compared. The acquisitions are stored in a memory area common to the different tasks and saved several times per hour. From these data and in parallel with the acquisitions, there are performed in continuous fashion the calculation of the parameters for an optimal instruction and its implementation on the feeding of the reactor, or on an alarm, as described above, in the event of malfunctioning of the system, or to act on other means or parameters used in a conventional manner in this type of application.

It is clear that the present invention is not limited to the examples of the embodiment described and/or mentioned here, but that it encompasses all variants thereof.

We claim:

1. A process for monitoring a device which removes pollutants from waste water by methane fermentation, comprising the steps:

simultaneously measuring three parameters of the gaseous phase in the digesters of a fermentation reactor, said parameters being,
(1) the total amount of gas present in a gaseous effluent from the reactor, produced during fermentation of organic material;
(2) the ratio of percentages of methane and carbon dioxide;
(3) hydrogen content; and processing the parameters, in real time, in order to verify proper functioning of the reactor.

2. The process according to claim 1 wherein said processing of the three parameters produces a signal for actuating an alarm device when the three parameters are indicative of an abnormal situation.

3. The method set forth in claim 1 wherein the measuring of the three parameters is performed by sensors located along a gas outlet pipe of the reactor.

* * * * *